United States Patent [19]

Ayad

[11] Patent Number: 4,767,773

[45] Date of Patent: Aug. 30, 1988

[54] SYNERGISTIC INSECTICIDAL COMPOSITIONS

[75] Inventor: Hafez M. Ayad, Cary, N.C.

[73] Assignee: Rhone-Poulenc Nederland B.V., Amstelveen, Netherlands

[21] Appl. No.: 830,898

[22] Filed: Jan. 3, 1986

Related U.S. Application Data

[63] Continuation of Ser. No. 393,554, Jun. 30, 1982, abandoned.

[51] Int. Cl.$^4$ .................... A01N 43/08; A01N 43/40; A01N 47/28
[52] U.S. Cl. .................................. 514/351; 514/469; 514/594
[58] Field of Search ................................ 514/351, 469

[56] References Cited

U.S. PATENT DOCUMENTS 3,748,356 7/1973 Wellinga et al. .
4,173,637 11/1979 Nishiyama et al. .
4,584,296 4/1986 Drabek et al. ...................... 514/147

FOREIGN PATENT DOCUMENTS 57-77604 5/1982 Japan .
2083360 3/1982 United Kingdom .

*Primary Examiner*—Allen J. Robinson
*Attorney, Agent, or Firm*—Morgan & Finnegan

[57] ABSTRACT

Insecticidal compositions are provided which contain mixtures of certain benzoyl ureas and pesticides.

The invention also encompasses a method of controlling insects by subjecting them to an effective amount of the synergistic insecticidal compositions.

2 Claims, No Drawings

SYNERGISTIC INSECTICIDAL COMPOSITIONS

This application is a continuation of prior U.S. application Ser. No. 393,554 June 30, 1982, now abandoned.

FIELD OF THE INVENTION

This invention relates, in general, to synergistic insecticidal compositions. In one aspect, this invention relates to compositions which contain certain benzoyl ureas in admixture with at least one pyrethroid, carbamate, organophosphate, chlorinated hydrocarbon, or a 2-aryl-1,3-cyclohexandione. In a further aspect, this invention relates to a method of controlling insects by the application of insecticidally effective amounts of the aforementioned compositions.

BACKGROUND OF THE INVENTION

It is known that combinations of certain pesticides with insect growth regulators provide synergistic kill of arthropods. For example, Plapp F. W. Jr., Journal of Economic Entomology, Volume 69, Number 1, pages 91–92, (1976), reported that chlordimeform synergized organophosphates, pyrethroids, a carbamate, a chlorinated hydrocarbon and diflubenzuron against larvae of an insecticide resistant population of Heliothis virescens (F). The prior art also teaches that mixtures of pesticides provide synergistic kill of arthropods. For example, U.S. Pat. No. 4,144,331 discloses synergistic combinations containing chlorofenvinphos and esters of carboxylic acid for control of diptera and ticks. European patent 0000962 A1 describes synergistic pesticidal compositions which comprise a pyrethroid insecticide and N,N-di-(2,4-xylyl-aminomethyl)-methylamine (also known as amitraz). It is claimed in U.S. Pat. Nos. 4,173,637 and 3,748,356 that mixtures of compounds described in these two patents with other insecticides, miticides and plant growth regulators, sometimes produce synergistic effects.

Although the aforementioned references indicate that a synergistic effect is obtained when certain compounds are combined with specific known insecticides, there is no broad teaching that such compounds would have the same effect when mixed with other insecticides.

For example, U.S. Pat. Nos. 4,173,637 and 3,748,356 previously mentioned, disclose that the mixtures of the compounds described in those two patents with other insecticides, miticides and plant growth regulators sometimes produce synergistic effects. However it has been observed that mixtures containing Dimilin or N-(2-chlorobenzoyl)N'-[4(3,5-dibromopyridyl-2-oxy)-phenyl]urea, two compounds described in U.S. Pat. Nos. 3,748,356 and 4,173,637, respectively, and piperonyl butoxide do not produce synergistic kill of many insects, such as the armyworm.

Moreover, to attempt to determine which synergist would be effective with which insecticide by a trial and error technique is beyond the economic capability of most research laboratories. Hence, it was indeed unexpected and surprising to find that certain pesticides were effective when employed in admixture with certain benzoyl urea insecticides. Thus, according to the present invention it was found that the amount of benzoyl urea insecticide can be greatly reduced resulting not only in economic savings but more importantly protecting the natural environment as well.

Accordingly, one or more of the following objects can be achieved by the practice of this invention. It is an object of this invention to provide novel insecticidal compositions which contain mixtures of a pesticide and certain benzoyl ureas. Another object of this invention is to provide insecticidal compositions containing mixtures of pyrethroids and cerain benzoyl ureas. A further object of this invention is to provide compositions containing mixtures of carbamates and certain benzoyl ureas. Another object is to provide insecticidal compositions containing mixtures of organophosphates and certain benzoyl ureas. A further object is to provide mixtures of chlorinated hydrocarbons and benzoyl ureas. Another object of this invention is to provide synergistic insecticidal compositions of 2-aryl-1,3-cyclohexandiones and benzoyl ureas. A still further object of the invention is to provide insecticidal compositions wherein the active toxicant can be employed in a reduced amount and still achieve the desired insect control. A still further object of the invention is to provide a method for controlling insect growth by the application of the compositions of this invention. Those and other objects will readily become apparent to those skilled in the art in the light of the teachings herein set forth.

SUMMARY OF THE INVENTION

In its broad aspect, the invention is directed to synergistic insecticidal compositions and to a method for their use. As indicated above, the synergistic insecticidal compositions of this invention are comprised of a mixture of a benzoyl urea and at least one pyrethroid, carbamate, organophosphate, chlorinated hydrocarbon, or a 2-aryl-1,3-cyclohexandione.

DETAILED DESCRIPTION OF THE INVENTION

As indicated above, the synergistic insecticidal composition of this invention are comprised of (a) a benzoyl urea component and (b) at least one other component which is a known pesticide.

The benzoyl urea component of the compositions of this invention encompasses compounds of the general structure:

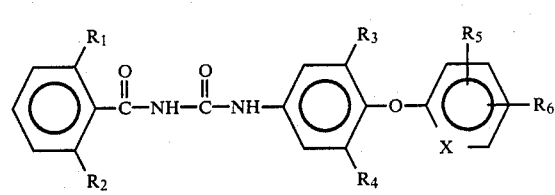

Wherein $R_1$ and $R_2$ are independently H, Cl, F, $OCH_3$ or $CH_3$; $R_3$ and $R_4$ are H, Cl or $CF_3$; R and $R_6$ are independently H, halogen, CN, $NO_2$ or $CF_3$, and X is CH or N.

Particularly useful composition of the general structure I are those wherein $R_1$ is chloro or fluoro, $R_2$ is hydrogen or fluoro, $R_3$ and $R_4$ are chloro and X is nitrogen. $R_5$ may be 3-chloro, and $R_6$ is 5-trifluoromethyl. When X is CH, $R_6$ may be 4-nitro.

Illustrative benzoyl ureas are compounds such as, 4-nitro-4'-[N-(N'-2-chlorobenzoyl)-ureido]-diphenyl ether, 4-nitro-2', 6'-dichloro-4'-[N(N'-2,6-difluorobenzoyl)ureido]-diphenyl ether, 4-nitro-4'-[N-(N'-2,6-difluorobenzoyl)-ureido]-diphenyl ether, 4-nitro-2,′,6′-dichloro-4′-[N-(N′-2-fluorobenzoylureido]-diphenyl ether, 4-nitro-2′,6′-dichloro-4′-[N-(N′-2-methylbenzoyl)ureido]-diphenyl ether, 4-nitro-2′,6′-dichloro-4′-[N′-2,6-dichlorobenzoyl)ureido]-diphenyl ether, N-(2,6-difluorobenzoyl)N′-4-(3-chloro-5-trifluoromethyl -pyridyl-2-oxy)phenyl]urea, N-(2,6-difluorobenzoyl)N′-[3,5-dichloro-4-(5-trifluoromethylpyridyl-2-oxy)phenyl]urea, N-(2,6-difluorobenzoyl)N′-[3,5-dichloro-4(3-chloro-5trifluoromethylpyridyl]-2-oxy) phenyl]urea, N-(2,6-difluorobenzoyl)N′-[3-chloro-4-(3-chloro-5-trifluoromethylpyridyl-2-oxy) phenyl]urea, N-(2-chlorobenzoyl)N′-4[3,5-dibromopyridyl-2-oxy)-phenyl]urea, and the like.

The benzoyl ureas employed in this invention are prepared by one or more procedures disclosed in the literature. For example, the 4-nitro-4′-[N-(N′benzoyl)-ureido]diphenyl ethers are prepared either by reacting a nitro-phenoxyaniline with a benzoyl isocyanate or by reacting a 4-isocyanato-diphenyl ether with a benzamide. Further details for the preparation of the nitro diphenyl ether derivatives are set forth in U.S. Pat. No. 4,041,177.

Benzoyl ureas wherein X in the above formulas is nitrogen can be prepared by the methods disclosed in U.S. Pat. No. 4,173,637. For example, a benzoyl isocyanate can be reacted with pyridyloxy aniline or a benzamide can be reacted with a pyridyloxy phenyl isocyanate.

The second component of the synergistic insecticidal compositions of this invention is a pesticide of the group of pyrethroids, carbamates, organophosphates, chlorinated hydrocarbons, and 2-aryl-1,3-cyclohexadiones These pesticides are of the following groups:

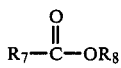
II wherein $R_7$ is:

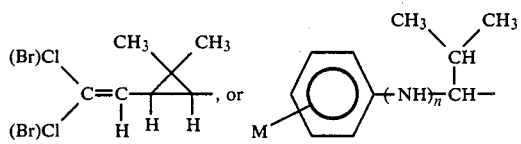

wherein $R_8$ is:

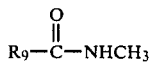

and M is Cl, $OCHF_2$ or $OCF_3$; n is zero or 1; and Z is H, $CH_3$, C≡CH or C≡N;

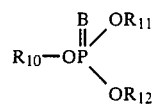
III wherein $R_9$ is alkylphenoxy, 1-naphthyl, 2,3-dihydro-2,2-dimethylbenzofuran-7-yl-oxy, 3,4,5-trimethylphenyl, 4-(methylthio)3,5-xylyl or 2,2-dimethyl-1,3-benzodioxol-4-yl. The carbonates, thiodicarb and methomyl can also be employed.

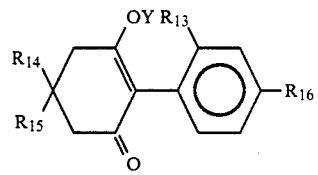
IV wherein B is O or S; $R_{10}$ is aryl or substituted aryl where the substituents may be one or more groups selected from nitro, chloro, bromo, alkylthio, alkylsulfinyl, alkyl or alkylsulfonyl; $R_{11}$ is lower alkyl, $R_{12}$ is alkyl, aryl or alkylthio, with the proviso that $R_{10}$, $R_{11}$, or $R_{12}$ individually may not contain more than 18 carbon atoms;

V wherein $R_{13}$ is lower alkyl, $R_{14}$, $R_{15}$ or $R_{16}$ are independently hydrogen or lower alkyl, and Y is an alkanoyl ester of 2 to 12 carbons; and Chlorinated aliphatic cycloaliphatic and aromatic hydrocarbons VI containing up to 8 chlorine atoms and up to 24 carbon atoms and which may optionally be substituted with up to 2 lower alkoxy groups or is hydropyl group.

Illustrative compounds encompassed by the above formulae include, but are not limited to, (permethrin) 3-(phenoxy-phenyl)methyl-3-(2,2-dichloroethenyl)-2,2-dimethyl cyclopropane carbonxylate; (fenvalerate) cyano(3-phenoxyphenyl) methyl-4-chloro-alpha-(1-methylethyl)benzene acetate; (BPMC) 2-(1-methyl propyl)phenyl methylcarbamate; (carbofuran)2,3-dihydro-2,2-dimethyl-7-benzofuranyl methylcarbamate; (carbaryl)1-naphthyl methyl carbamate; (thiodicarb) dimethyl-N,N′-[thiobis (methyliminocarbonyloxy)] bis[ethanimidiothioate ]; (methomyl)methyl (methyliminocarbonyloxy)ethanimidothioate; (malathion) 0,0-dimethylphosphorodithioate of diethyl mercaptosuccinate; (methyl-parathion) 0,0-dimethyl-0-p-nitrophenylphosphorothioate; (acephate) O,S-dimethyl acetylphosphoramidothioate; (azinophos-methyl) O,O-dimethyl S-[4-oxo-1,2,3-benzotriazin-3(4H)-yl) methyl] phosphorodithioate; (profenofos) 0-(4-bromo-2-chlorophenyl)-0-ethyl-S-propyl-phosphorothioate; 3-(2-ethylhexanoyloxy)-5,5-dimethyl-2-(2′methylphenyl)-1-cyclohexanone; 3-(ethylhexanoyloxy) 5,5-dimethyl-2-(2′,4′-dimethylphenyl)-2-cyclohexane; (DDT) 1,1,1-trichloro-2,2-bis-(p-chlorophenyl)ethane; (dicofol) 4-chloro-alpha-(4-chlorophenyl)-alpha-(trichloromethyl)-benzenemethanol; (methoxychlor) 2,2-bis(p-methoxyphenyl)-1,1,1-trichloroethane; (chlordome) 1,2,4,5,6,7,8-octachloro-2,5,3a,4,7,7a-hexahydro-4,7-methano-(H-indene); and (Lindane) hexachlorocyclohexane and the like.

The proportion of the benzoylureas to the pesticide can vary over a wide range depending on such factors as the particular locus to be treated, the particular pest to be combatted and the particular effect desired. The weight proportion of the benzoylurea to the pesticide may be, for example, from 1:0.5 to 1:1000, respectively.

Usually there is a greater proportion of pesticide than the benzoylurea. Preferably, the proportion of pesticide to the benzoylurea are 5:1 to 500:1, respectively.

In the practice of the novel compositions of the present invention, the pesticide is mixed with the benzoylurea and a suitable inert carrier which may be a solid or a liquid. One suitable method of preparing the compositions of the present invention is to mix the pesticide with or without solvent or diluent, with a suitable carrier and then mix the resulting composition with the benzoylurea with or without solvent.

The novel pesticidal compositions of the present invention will typically include conventional pest control adjuvants, diluents, modifiers or conditioning agents, herein included in the term "suitable carrier substance", to provide compositions in the form of solutions, emulsions, dispersions, powders, dusts, granules pellet and the like. Thus, the pesticidal compositions can be either liquids or solids. The liquid compositions can contain one or more surface active agents as a conditioning agent to render the composition readily dispersable in water. The term surface active agents includes wetting agents, dispersing agents, emulsifying agents and the like. The solid formulations of the present invention in the form of powder, dust, pellets or granules can be prepared using such substances as talc, natural clay, pyrophyllite, diatomaceous earth, walnut shells, corn cobs, sugar, sand and the like.

Suitable liquid diluents or carriers include water, petroleum distillates, or other liquid carriers with or without surface active agents. Liquid concentrates may be prepared by dissolving one of these compositions with a non-phytoxic solvent such as acetone, xylene, or nitro-benzene and dispersing the toxicants in water with the aid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, or cationic dispersing and emulsifying agents, for example, the condensation products of alkylene oxides with phenol and organic acids, alkyl aryl sulfonates, complex ether alcohols, quaternary ammonium compounds, and the like may be employed for this purpose.

In the preparation of wettable powder or dust or granulated compositions, the active ingredient is dispersed in and on an appropriately divided solid carrier such as natural clay, talc, pyrophyllite, bentonite, diatomaceous earth, fullers earth, corn cobs, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 10 to 95 percent by weight. Satisfactory sprays, dust, or granules for general use contain from about $\frac{1}{4}$ to 15 pounds of active toxicant per acre.

The insecticides contemplated herein prevent attachment by insects upon plants or other material to which the insecticides are applied. With respect to plants, they have a high margin of safety in that when used in sufficient amount to kill or repel the insects, they do not burn or injure the plant, and they resist weathering which includes wash-off caused by rain, decomposition by ultra-violet light, oxidation, or hydrolysis in the presence of moisture or, at least, such decomposition, oxidation, and hydrolysis as would materially decrease the desirable insecticidal characteristics of the toxicants or impart undesirable characteristics, for instance, phototoxicity, to the toxicants. The toxicants are compatible with other constituents of the spray schedule, and they may be used in the soil, upon the seeds, or the roots of plants. Mixtures of the synergistic insecticidal compositions of this invention may be employed if desired as well as combinations of the synergistic insecticidal compositions with one or more fungicides, bactericides, acaricides, nematicides, insecticides or other biologically active compounds.

The synergistic insecticidal compositions of this invention are effective against a wide variety of insects. It is understood that the Southern armyworm evaluated in the working Examples herein is representative of a wider variety of insect which can be controlled by the synergistic insecticidal compositions of this invention. These compositions are particularly useful in controlling insects of agricultural crops, e.g., potatoes, maize, sugar beets, cotton, rice, wheat, tobacco, soybeans, deciduous and citrus fruits.

The joint action of the two pesticides employed in the insecticidal composition of this invention was analyzed according to the method of Yun-Pei Sun and E. R. Johnson, Journal of Economic Entomology, 1960, Volume 52, No. 5, pages 887-892.

Thus, the join action of two pesticides was analyzed by determining the actual toxicity indices of the components and of mixtures of the compounds by reference to dosage-mortality curves. The theoretical toxicity of the mixture is equal to the sum of toxicity indices calculated from the percentage of each component multiplied by its respective toxicity index. Therefore, the joint toxicity:

$$\text{Co—toxicity co-efficient of a mixture} = \frac{\text{Actual Toxicity of a mixture}}{\text{Theoretical toxicity index of a mixture}} \times 100$$

A coefficient of a mixture near 100 indicates probability of similar action by the two pesticides; independent action usually, should give a coefficient less than 100, while coefficient significantly above 100 strongly indicates synergism.

The following examples illustrate the best mode presently contemplated for the practice of this invention:

EXAMPLE 1

Use of a mixture of N-(2,6 difluorobenzoyl)-N'-[3,5-dichloro-4-(3-chloro-5-trifluoromethyl pyridyl-2-oxy)phenyl]urea and other pesticides for control of Southern armyworm larvae (Spodoptera eridania Aqueous suspension of benzoylurea and pesticides listed in Table 1 were prepared by dissolving 1 gram of each compound in 50 milliliters of acetone in which had been dissolved 0.1 gram (10 percent by weight of each compound to be tested) of an alkylphenoxy polyethyoxyethanol surfactant as an emulsifying or dispersing agent. The resulting solutions were mixed with 150 milliliters of water to give 200 milliliters of a suspension containing each test compound in finely divided form. The thus-prepared stock suspension contained 0.5 percent by weight of each compound. The concentration employed in the test results presented below were obtained by diluting the stock suspensions with water. Potted tendergreen bean plants of standard height and age were placed on a revolving turntable and sprayed with 100-110 milliliters of test compound formulation by use of a De Vilbiss spray gun set at 40 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°-85° F. for three days. Although the larvae could easily consume the whole leaf within twenty-four hours, no more food was added. Larvae which were unable to move the length of the body, even upon stimulation by prodding, were considered dead. Per cent mortality was recorded for the various concentration levels. $LD_{50}$ (concentration required to kill 50 per cent of the armyworm larvae) volume were determined from the mortality figures.

The results of these tests are set forth in Table 1 below:

TABLE I

TOXICITY TO ARMYWORM LARVAE

| Compound or Compound mixture | Weight ratio of mixture | $LD_{50}$(ppm) Spodoptera eridania | Coefficient of co-toxicity | Synergistic ratio [1] |
|---|---|---|---|---|
| A[2] | 1:67 | 0.7 | 8794 | |
| malathion | | 140 | | |
| A + malathion methyl-parathion | | 0.4 22 | | |
| A + methyl-parathion profenofos | 1:6 | 0.1 9 | 4184 | |
| A + profenofos acephate | 1:16 | 0.4 11 | 1326 | |
| A + acephate azinophosmethyl | 1:40 | 0.5 30 | 1628 | |
| A + azinophos-methyl chlorpyriphos | 1:30 | 0.16 11 | 8102 | |
| A + chlorpyriphos carbofuran | 1:16 | 0.19 34 | 3096 | |

TABLE I-continued

TOXICITY TO ARMYWORM LARVAE

| Compound or Compound mixture | Weight ratio of mixture | $LD_{50}$(ppm) Spodoptera eridania | Coefficient of co-toxicity | Synergistic ratio [1] |
|---|---|---|---|---|
| A + carbofuran carbaryl | 1:100 | 0.25 96 | 9091 | |
| A + carbaryl thiodicarb | 1:50 | 0.7 4.3 | 3676 | |
| A + thiodicarb methomyl | 1.5:5 | 0.7 7 | 241 | |
| A + methomyl BPMC | 1:5 | 1.0 500 | 250 | |
| A + BPMC fenvalerate | 1:500 | 0.2 5.0 | — | 3.5 |
| A + fenvalerate permethrin | 1.5:5 | 0.8 5.0 | 220 | |
| A + permethrin DDT | 1.5:5 | 1.2 31 | 147 | |
| A + DDT dicofol | 1:25 | 0.04 200 | 28363 | |
| A + dicofol methoxychlor | 1:25 | 0.28 140 | 5760 | |
| A + methoxychlor 3-(2-ethylhexanoyloxy)-5,5-dimethyl-2-(2'-methylphenyl)-1-cyclohexanone | 1:25 | 0.37 500 | 4223 | — |
| A + 500 ppm of preceding compound 3-(2-ethylhexanoyloxy)-5,5-dimethyl-2-(2'-4'-dimethylphenyl)-2-cyclohexanone | | 0.28 500 | — | 2.3 |
| A + 500 ppm of same preceding compound | | 0.23 | — | 3.0 |

[1]Synergistic ratio = $\frac{LD_{50} \text{ of compound A alone}}{LD_{50} \text{ of the mixture}}$

[2]A = N—(2,6 difluorobenzoyl)N'—[3,5-dichloro-4-(3-chloro-5-trifluoromethyl-pyridyl-2-oxy)phenyl]urea.

Although the invention has been illustrated by the foregoing examples, it is not to be construed as being limited to the materials employed therein; but rather, the invention encompasses the generic area as hereinafter disclosed. Various modifications and embodiments can be made without departing from the spirit and scope thereof.

What is claimed is:

1. A synergistic insecticidal composition comprising N-(2,6-difluorobenzoyl)-N-[3,5-dichloro-4-(3-chloro-5-trifluoromethylpyridyl-2-oxy)phenyl]urea and 2,3-dihydro-2,2-dimethyl-7-benzofuranyl methylcarbamate wherein the weight proportion ratio of N-(2,6-difluorobenzoyl)-N-[3,5-dichloro-4-(3-chloro-5-trifluoromethylpyridyl-2-oxy)phenyl]urea to 2,3-dihydro-2,2-dimethyl-7-benzofuranyl methylcarbamate is from 1:0.5 to 1:1000.

2. A method of controlling insects which comprises subjecting said insects to an insecticidally effective amount of the synergistic insecticidal composition of claim 1.

* * * * *